United States Patent
Kasai et al.

(10) Patent No.: US 9,434,737 B2
(45) Date of Patent: Sep. 6, 2016

(54) PROCESS FOR PRODUCING OPTICALLY ACTIVE SUCCINIMIDE DERIVATIVES AND INTERMEDIATES THEREOF

(71) Applicants: Dainippon Sumitomo Pharma Co., Ltd., Osaka-shi (JP); Kyowa Hakko Bio Co., Ltd., Tokyo (JP)

(72) Inventors: Masaji Kasai, Takaoka (JP); Shinji Kita, Takaoka (JP); Tadashi Ogawa, Takaoka (JP); Hideaki Tokai, Takaoka (JP)

(73) Assignees: Sumitomo Dainippon Pharma Co., Ltd., Osaka (JP); Kyowa Hakko Bio Co., Ltd., Tokyo (JP)

( * ) Notice: Subject to any disclaimer, the term of this patent is extended or adjusted under 35 U.S.C. 154(b) by 42 days.

(21) Appl. No.: 14/104,597

(22) Filed: Dec. 12, 2013

(65) Prior Publication Data

US 2014/0099681 A1   Apr. 10, 2014

Related U.S. Application Data

(62) Division of application No. 13/148,263, filed as application No. PCT/JP2010/000695 on Feb. 5, 2010, now Pat. No. 8,633,001.

(30) Foreign Application Priority Data

Feb. 6, 2009 (JP) ................. 2009-025599

(51) Int. Cl.
| | |
|---|---|
| C07D 487/20 | (2006.01) |
| C07C 271/22 | (2006.01) |
| C07D 207/416 | (2006.01) |
| C12P 7/62 | (2006.01) |
| C12P 17/10 | (2006.01) |
| C12P 41/00 | (2006.01) |
| C12P 17/18 | (2006.01) |

(52) U.S. Cl.
CPC ........... *C07D 487/20* (2013.01); *C07C 271/22* (2013.01); *C07D 207/416* (2013.01); *C12P 7/62* (2013.01); *C12P 17/10* (2013.01); *C12P 17/182* (2013.01); *C12P 41/005* (2013.01); *C07B 2200/07* (2013.01)

(58) Field of Classification Search
None
See application file for complete search history.

(56) References Cited

U.S. PATENT DOCUMENTS

| | | |
|---|---|---|
| 7,994,342 B2 | 8/2011 | Kudo et al. |
| 2010/0003729 A1 | 1/2010 | Kudo et al. |
| 2011/0190497 A1 * | 8/2011 | Tanaka ................ C07D 487/20 544/231 |

FOREIGN PATENT DOCUMENTS

| | | | |
|---|---|---|---|
| JP | 05-186472 A | 7/1993 | |
| JP | 06-192222 A | 7/1994 | |
| JP | 10-245369 A | 9/1998 | |
| JP | WO 2008038646 A1 * | 4/2008 | ......... C07D 207/416 |
| WO | WO 2008/035735 A1 | 3/2008 | |

OTHER PUBLICATIONS

Machine Translation of JP06-192222, Jul. 12, 1994, p. 1-23.*
Conde et al., *Eur. J. Org. Chem.*, 2002(5): 922-929 (2002).
Haberhauer et al., *Tetrahedron Letters*, 41(26): 5013-5016 (2000).
Nakayama et al., *Bioorganic & Medicinal Chemistry*, 5(5): 971-985 (1997).
Negoro et al., *Journal of Medicinal Chemistry*, 41: 4118-4129 (1998).
Sano et al., *Tetrahedron Letters*, 39(31): 5571-5574 (1998).
Japanese Patent Office, International Search Report for International Application No. PCT/JP2010/000695 (Mar. 16, 2010).
Japanese Patent Office, International Preliminary Report on Patentability for International Application No. PCT/JP2010/000695 (Sep. 13, 2011).
U.S. Appl. No. 13/148,263, filed Aug. 5, 2011.

* cited by examiner

*Primary Examiner* — Paul Holland
(74) *Attorney, Agent, or Firm* — Leydig, Voit & Mayer, Ltd.

(57) ABSTRACT

Provided is a process for producing (3R)-2'-(4-bromo-2-fluorobenzyl)spiro{pyrrolidine-3,4'(1'H)-pyrrolo[1,2-a]pyrazine}-1',2,3',5(2'H)-tetraone (compound A). The method includes converting an optically active succinimide derivative of formula (I) to compound A, in which the compound of formula (I) has been prepared by reacting a base with an optically active amide derivative of formula (VI).

8 Claims, No Drawings

PROCESS FOR PRODUCING OPTICALLY ACTIVE SUCCINIMIDE DERIVATIVES AND INTERMEDIATES THEREOF

CROSS-REFERENCE TO RELATED APPLICATIONS

This patent application is a divisional of copending U.S. patent application Ser. No. 13/148,263, now U.S. Pat. No. 8,633,001, filed on Aug. 5, 2011, which is the U.S. national phase of International Patent Application No. PCT/JP2010/000695 filed on Feb. 5, 2010, which claims the benefit of Japanese Patent Application No. 2009-025599, filed on Feb. 6, 2009, each of which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 26,041 bytes ASCII (Text) file named "715624SequenceListing.txt," created Dec. 9, 2013.

TECHNICAL FIELD

The present inventions relates to a process for producing optically active succinimide derivatives as key intermediates of (3R)-2'-(4-bromo-2-fluorobenzyl)spiro{pyrrolidine-3,4'(1'H)-pyrrolo[1,2-a]pyrazine}-1',2,3',5(2'H)-tetraone (henceforth referred to as "compound A" in this specification) represented by the following formula, which is expected to be a therapeutic agent for diabetic complications.

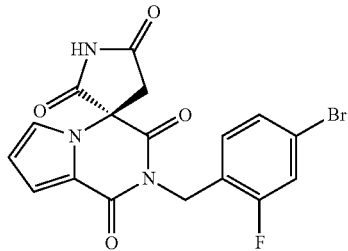

(Compound A)

The present invention also relates to an ester derivative, optically active carboxylic acid derivative, and optically active amide derivative, which are useful intermediates of the compound A mentioned above, as well as processes for producing thereof and a process for producing the compound A by using said derivatives.

BACKGROUND ART

Methods for dividing a racemate into optical isomers (optical resolution methods) include a method of using an enzyme, a method of reacting optical isomers for conversion into salts and dividing the salts, a method of preparing a diastereomer mixture by reactions with optical isomers and then purifying the mixture for separation, and the like. Among them, the method of using an enzyme does not require optical isomers, and accordingly the method is advantageous since the reaction can be performed at low cost, for example. However, said method also has a problem that it is generally difficult to regioselectively and stereoselectively hydrolyze a specific alkoxycarbonyl of a triester or the like having two or more alkoxycarbonyls in a single molecule.

As methods for producing an optically active carboxylic acid derivative by regioselective and stereoselective hydrolysis using an esterase, Patent document 1 and Non-patent documents 1 and 2 report methods of asymmetrically hydrolyzing an α-(lower alkyl)-α-(protected amino)malonate diester derivative by using a pig liver esterase to produce an optically active α-(lower alkyl)-α-(protected amino)malonate monoester derivative.

[Formula 2]

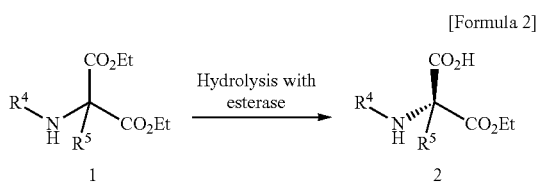

(In the formulas, $R^4$ represents benzyloxycarbonyl, tert-butoxycarbonyl, or the like, and $R^5$ represents a lower alkyl or the like.)

Patent document 2 describes a method for producing (R)-2-amino-2-ethoxycarbonylsuccinimide (henceforth referred to as compound B), which is a key intermediate of the compound A, by using an esterase.

Methods for preparing the compound A from the compound B are described in Patent document 3, Non-patent document 3, and the like, and a method of preparing 4-tert-butyl 1-ethyl 2-benzyloxycarbonylamino-2-ethoxycarbonylsuccinate by reacting diethyl 2-benzyloxycarbonylaminomalonate and tert-butyl 2-bromoacetate is described in Reference Example 1 of Patent document 4.

PRIOR ART REFERENCES

Patent Documents

Patent document 1: Japanese Patent Unexamined Publication (Kokai) No. 10-245369
Patent document 2: International Patent Publication WO2008/035735
Patent document 3: Japanese Patent Unexamined Publication No. 05-186472
Patent document 4: Japanese Patent Unexamined Publication No. 06-192222

Non-Patent Documents

Non-patent document 1: Tetrahedron Letters (Tetrahedron Lett.), 1998, 39 (31), 5571-5574
Non-patent document 2: Tetrahedron Lett., 2000, 41 (26), 5013-5016
Non-patent document 3: Journal of Medicinal Chemistry (J. Med. Chem.), 1998, 41, pp. 4118-4129

SUMMARY OF THE INVENTION

Object to be Achieved by the Invention

An object of the present invention is to provide a process for producing optically active succinimide derivatives as key intermediates of the compound A.

Another object of the present invention is to provide an ester derivative, an optically active carboxylic acid derivative, and an optically active amide derivative, which are useful intermediates of the compound A, as well as processes for producing thereof and a process for producing the compound A by using said derivatives.

Means for Achieving the Object

The present invention relates to the following (1) to (16).

(1) A process for producing an optically active succinimide derivative represented by the formula (I):

[Formula 3]

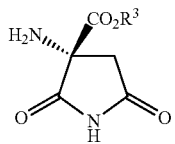

[in the formula (I), $R^3$ represents a lower alkyl] or a salt thereof, which comprises the following steps (A) to (D), and further comprises the step (E), if necessary:

(A) the step of reacting an aminomalonate derivative represented by the formula (II):

[Formula 4]

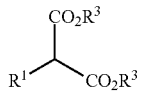

[in the formula (II), $R^1$ represents amino or an amino protected with a protective group, and two of $R^3$ represent the same lower alkyls having the same meaning as that defined above] and a halogenated acetic acid ester derivative represented by the formula (III):

[Formula 5]

$$Y\text{---}CH_2CO_2R^2 \quad (III)$$

[in the formula (III), $R^2$ represents a lower alkyl, and Y represents a halogen] in the presence of a base for conversion into an ester derivative represented by the formula (IV):

[Formula 6]

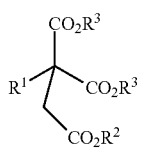

[in the formula (IV), each of $R^1$, $R^2$, and $R^3$ has the same meaning as that defined above] or a salt thereof, (B) the step of allowing an enzyme to react on the ester derivative represented by the formula (IV) or a salt thereof to convert the ester into an optically active carboxylic acid derivative represented by the formula (V):

[Formula 7]

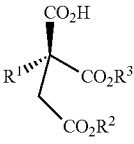

[in the formula (V), each of $R^1$, $R^2$, and $R^3$ has the same meaning as that defined above] or a salt thereof, (C) the step of reacting the optically active carboxylic acid derivative represented by the formula (V) or a salt thereof with an ammonia source in the presence of a condensing agent, or reacting the optically active carboxylic acid derivative represented by the formula (V) or a salt thereof with an activating reagent and then reacting the resultant with an ammonia source for conversion into an optically active amide derivative represented by the formula (VI):

[Formula 8]

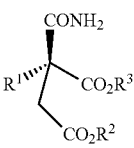

[in the formula (VI), each of $R^1$, $R^2$, and $R^3$ has the same meaning as that defined above] or a salt thereof, (D) the step of allowing a base to react on the optically active amide derivative represented by the formula (VI) or a salt thereof for conversion into an optically active succinimide derivative represented by the formula (I) or (VII):

[Formula 9]

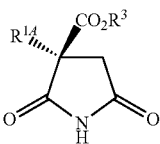

[in the formula (VII), $R^{1A}$ represents an amino protected with a protective group, and $R^3$ has the same meaning as that defined above] or a salt thereof, and (E) the step of eliminating the protective group on $R^{1A}$ of the optically active succinimide derivative represented by the formula (VII) or a salt thereof for conversion into an optically active succinimide derivative represented by the aforementioned formula (I) or a salt thereof.

(2) A process for producing an ester derivative represented by the formula (IV-A):

[Formula 11]

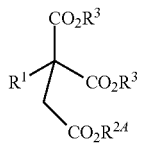
(IV-A)

[in the formula (IV-A), each of $R^1$, $R^{2A}$, and $R^3$ has the same meaning as that defined above]
or a salt thereof, which comprises the step of allowing a halogenated acetic acid ester derivative represented by the formula (III-A):

[Formula 10]

$$Y—CH_2CO_2R^{2A} \quad \text{(III-A)}$$

[in the formula (III-A), $R^{2A}$ represents a lower alkyl selected from methyl, ethyl, propyl, isopropyl, butyl, isobutyl, sec-butyl, pentyl, isopentyl, neopentyl and hexyl, and Y has the same meaning as that defined above]
to react on an aminomalonate derivative represented by the formula (II) in the presence of a base.

(3) A process for producing an optically active carboxylic acid derivative represented by the formula (V) or a salt thereof, which comprises the step of allowing an enzyme to react on an ester derivative represented by the formula (IV) or a salt thereof.

(4) The production process according to (1) or (3), wherein the enzyme is a pig liver esterase or a rabbit liver esterase.

(5) A process for producing an optically active amide derivative represented by the formula (VI) or a salt thereof, which comprises the step of reacting an optically active carboxylic acid derivative represented by the formula (V) or a salt thereof with an activating reagent, and further reacting the resultant with an ammonia source.

(6) A process for producing an optically active amide derivative represented by the formula (VI) or a salt thereof, which comprises the step of reacting an optically active carboxylic acid derivative represented by the formula (V) or a salt thereof with an ammonia source in the presence of a condensing agent.

(7) A process for producing an optically active succinimide derivative represented by the formula (I) or the formula (VII) or a salt thereof, which comprises the step of allowing a base to react on an optically active amide derivative represented by the formula (VI) or a salt thereof.

(8) The production process according to any one of (1) to (7), wherein $R^1$ and $R^{1A}$ mentioned in (1), (4) or (7), or $R^1$ mentioned in any one of (2) to (6) is benzyloxycarbonylamino, $R^2$ mentioned in (1) or any one of (3) to (7), or $R^{2A}$ mentioned in (2) is ethyl, and $R^3$ mentioned in any one of (1) to (7) is ethyl.

(9) An ester derivative represented by the formula (IV-A):

[Formula 12]

(IV-A)

[in the formula (IV-A), $R^1$ represents amino or an amino protected with a protective group, $R^{2A}$ represents a lower alkyl selected from methyl, ethyl, propyl, isopropyl, butyl, isobutyl, sec-butyl, pentyl, isopentyl, neopentyl and hexyl, and two of $R^3$ represent the same lower alkyls having the same meaning as that defined above] or a salt thereof.

(10) An optically active carboxylic acid derivative represented by the formula (V):

[Formula 13]

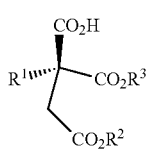
(V)

[in the formula (V), $R^2$ represent a lower alkyl, and each of $R^1$ and $R^3$ has the same meaning as that defined above] or a salt thereof.

(11) An optically active amide derivative represented by the formula (VI):

[Formula 14]

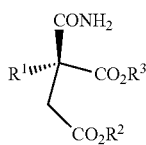
(VI)

[in the formula (VI), each of $R^1$, $R^2$, and $R^3$ has the same meaning as that defined above] or a salt thereof.

(12) The derivative according to (9), wherein $R^1$ is benzyloxycarbonylamino, and $R^{2A}$ and $R^3$ are ethyls.

(13) The derivative or a salt thereof according to (10) or (11), wherein $R^1$ is benzyloxycarbonylamino, and $R^2$ and $R^3$ are ethyls.

(14) A process for producing the compound A, which comprises the step of producing an optically active succinimide derivative represented by the formula (I) {henceforth referred to as compound (I)} by the production process according to (1) or (7), and the step of converting the compound (I) obtained in the above step into the compound A.

(15) A process for producing the compound A, which comprises the following steps (a) to (e):
(a) the step of producing the compound (I) by the method according to (1), (7) or (8);
(b) the step of reacting the compound (I) obtained in the step (a) with 2,5-dimethoxytetrahydrofuran in the presence of an acid (for example, acetic acid and the like);

(c) the step of reacting the product obtained in the step (b) with a trichloroacetylating reagent (for example, trichloroacetyl chloride, trichloroacetyl bromide, trichloroacetic anhydride, and the like);

(d) the step of reacting the product obtained in the step (c) with 4-bromo-2-fluorobenzylamine; and (e) the step of isolating the compound A obtained in the step (d).

(16) The production process according to (14) or (15), wherein $R^3$ is ethyl.

Effect of the Invention

By using the intermediates and the production processes thereof according to the present invention, the compound (I) useful as an intermediate of the compound A and the compound A can be efficiently synthesized. In particular, the compound (I) and the compound A of high optical purity can be produced at a high yield according to the processes of the present invention, and therefore, they are advantageous from an industrial viewpoint and the like

MODES FOR CARRYING OUT THE INVENTION

It is defined above that the compound represented by the formula (I) is referred to as the compound (I), and such designation scheme is henceforth also applied to the compounds of the other formula numbers.

In the definitions of the groups included in the formulas (I) to (VII), (III-A), and (IV-A):

examples of the lower alkyl include, for example, a linear or branched alkyl having 1 to 6 carbon atoms, more specifically, methyl, ethyl, propyl, isopropyl, butyl, isobutyl, sec-butyl, tert-butyl, pentyl, isopentyl, neopentyl, hexyl, and the like. The halogen means an atom of fluorine, chlorine, bromine, or iodine.

Examples of the protective group of the "amino protected with a protective group" include, for example, protective groups for amino usually used in the organic synthesis chemistry [for example, those described in T. W. Greene, Protective Groups in Organic Synthesis, third edition, John Wiley & Sons Inc. (1999), and the like], and more preferred examples include such protective groups that can be deprotected by an action of a thiol or an acid, hydrogenolysis, or the like.

Examples of the protective group that can be deprotected by an action of a thiol include, for example, 2-nitrobenzenesulfonyl, 4-nitrobenzenesulfonyl, 2,4-dinitrobenzenesulfonyl, and the like.

Examples of the protective group that can be deprotected by an action of an acid include, for example, acetyl, trityl, tert-butoxycarbonyl, and the like, and more preferred examples include tert-butoxycarbonyl.

Examples of the protective group that can be deprotected by hydrogenolysis include, for example, benzyloxycarbonyl, benzyl and the like, which may have 1 to 3 substituents selected from the group consisting of a halogen atom, lower alkyl, lower alkoxyl and nitro on the benzene ring. More preferred examples include benzyloxycarbonyl, 4-nitrobenzyloxycarbonyl, 4-chlorobenzyloxycarbonyl, 4-methylbenzyloxycarbonyl, 2-methoxybenzyloxycarbonyl, benzyl, 4-nitrobenzyl, 4-chlorobenzyl, 4-methylbenzyl, 2-methoxybenzyl, 4-methoxybenzyl, and the like.

In the present invention, the amino protected with a protective group may be converted into amino during the reaction.

Examples of $R^1$ and $R^{1A}$ in the formulas include, for example, an amino protected with a protective group that can be deprotected by an action of a thiol or an acid, or hydrogenolysis, and the like, and preferred examples include benzyloxycarbonylamino and tert-butoxycarbonylamino.

Examples of $R^2$ and $R^3$ in the formulas include, for example, ethyl, and the like. Examples of $R^{2A}$ also include, for example, ethyl, and the like.

Examples of preferred combination of $R^1$, $R^2$ and $R^3$ include, for example, such a combination that $R^1$ is benzyloxycarbonylamino, and $R^2$ and $R^3$ are ethyls. Examples of preferred combination of $R^1$, $R^{2A}$ and $R^3$ include, for example, such a combination that $R^1$ is benzyloxycarbonylamino, and $R^{2A}$ and $R^3$ are ethyls. Examples of preferred combination of $R^{1A}$ and $R^3$ include, for example, such a combination that $R^{1A}$ is benzyloxycarbonylamino and $R^3$ is ethyl.

Examples of Y include a halogen, and preferred examples include iodine, bromine, chlorine, and the like. More preferred examples include bromine and chlorine.

Examples of the ammonia source include ammonia, an ammonia equivalent, and the like, and preferred examples include ammonia. Examples of the form of ammonia include gas or aqueous solution, and preferred examples include aqueous solution.

Examples of the ammonia equivalent include, for example, a salt of ammonia and an acid, preferred examples include ammonium acetate, ammonium formate, and ammonium carbonate, and more preferred examples include ammonium acetate.

Examples of the condensing agent include, for example, dicyclohexylcarbodiimide (DCC), 1-ethyl-3-(3-dimethylaminopropyl)carbodiimide hydrochloride, N,N'-carbonyldiimidazole (CDI), N-hydroxybenzotriazole (HOBT), diphenylphosphoric acid azide (DPPA), N-hydroxysuccinimide, N-hydroxyphthalimide, benzotriazol-1-yloxytrisdimethylaminophosphonium hexafluorophosphate (BOP), 4-(4,6-dimethoxy-1,3,5-triazin-2-yl)-4-methylmorpholinium chloride (DMTMM), O-(benzotriazol-1-yl)-N,N,N',N'-tetramethyluronium hexafluorophosphate (HBTU), 2-chloro-1-methylpyridinium iodide, and the like.

Examples of the activating reagent include, for example methyl chloroformate, ethyl chloroformate, isopropyl chloroformate, isobutyl chloroformate, pivaloyl chloride, phosgene, triphosgene, phosphorus oxychloride, phosphorus pentachloride, thionyl chloride, and the like, and preferred examples include isobutyl chloroformate.

Examples of the salt of the compound (I), (IV), (V), (VI), (VII) or (IV-A) include, for example, an acid addition salt, metal salt, ammonium salt, organic amine addition salt, amino acid addition salt, and the like. Examples of the acid addition salt include, for example, an inorganic acid salt such as hydrochloride, hydrobromide, nitrate, sulfate, and phosphate, organic acid salt such as acetate, oxalate, maleate, fumarate, citrate, benzoate and methanesulfonate, and the like. Examples of the metal salt include, for example, an alkali metal salt such as sodium salt and potassium salt, alkaline earth metal salt such as magnesium salt and calcium salt, aluminum salt, zinc salt, and the like. Examples of the ammonium salt include, for example, salts of ammonium, tetramethylammonium, and the like, and examples of the organic amine addition salt include addition salts of morpholine, piperidine, and the like. Examples of the amino acid addition salt include, for example, addition salts of lysine, glycine, phenylalanine, aspartic acid, glutamic acid, and the like.

The production processes of the present invention will be explained below. However, the reaction conditions such as reaction temperatures, types of reagents, amounts of reagents and reaction times are mentioned merely for exemplification, and they should not be construed any limitative way.

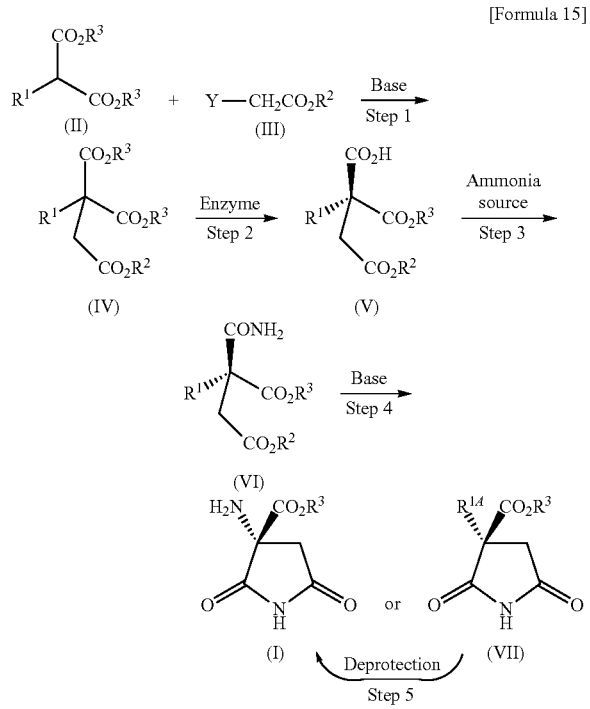

[Formula 15]

(In the formulas, $R^1$ represents amino or an amino protected with a protective group, $R^{1.4}$ represents an amino protected with a protective group, $R^2$ and $R^3$ are the same or different, and represent a lower alkyl, and Y represents halogen.)

(Step 1)

By reacting one equivalent to a large excess amount of the compound (III) with the compound (II) in a solvent at a temperature of −50 to 150° C. for 5 minutes to 72 hours in the presence of 1 to 30 equivalents of a base, the compound (IV) can be obtained. The reaction may be performed with addition of an alkali halide.

As the solvent, any solvent that does not participate in the reaction may be used. Examples include cyclohexane, benzene, toluene, xylene, diethyl ether, diisopropyl ether, tert-butyl methyl ether, tetrahydrofuran (THF), dioxane, pyridine, methanol, ethanol, isopropyl alcohol, dimethylformamide (DMF), dimethyl sulfoxide (DMSO), acetonitrile, and the like, and preferred examples include DMF. These can be used independently or as a mixture.

Examples of the base include an organic base and an inorganic base, preferred examples include an inorganic base, more preferred examples include sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like, still more preferred examples include sodium hydride, sodium carbonate, sodium hydrogencarbonate, potassium carbonate, potassium hydrogencarbonate, cesium carbonate, and the like, and most preferred examples include sodium hydride and potassium carbonate.

Examples of the alkali halide include an alkali bromide, an alkali iodide, and the like, preferred examples include an alkali iodide, and more preferred examples include lithium iodide, sodium iodide, potassium iodide, and cesium iodide. Most preferred examples include potassium iodide.

Examples of the compound (III) include ethyl 2-chloroacetate, ethyl 2-bromoacetate, and the like.

The compound (II) and the compound (III) can also be obtained as marketed products.

(Step 2)

By allowing an enzyme in an amount of 1/100,000 to 10-fold, preferably 1/10,000 to 1-fold, based on the substrate to react on the compound (IV) in water or a mixed solvent of water and a solvent at a substrate concentration of 0.1 to 50%, preferably 1 to 30%, a temperature of 0 to 60° C., preferably 10 to 40° C., and a reaction pH of 3 to 10, preferably 4 to 9, to allow the reaction for 1 to 200 hours, preferably 5 to 150 hours, the compound (V) can be obtained. The reaction can also be performed with adding a buffer or a metal salt.

Examples of the solvent include cyclohexane, benzene, toluene, xylene, diethyl ether, diisopropyl ether, tert-butyl methyl ether, THF, dioxane, methyl acetate, ethyl acetate, butyl acetate, methyl isobutyl ketone, acetone, dichloromethane, chloroform, dichloroethane, carbon tetrachloride, methanol, ethanol, isopropyl alcohol, tert-butyl alcohol, DMF, DMSO, acetonitrile, and the like, and preferred examples include ethanol and acetonitrile. When a mixed solvent is used, the solvent may form a homogeneous system or a heterogeneous system of water and a solvent, and the solvent preferably forms such a homogeneous system.

Examples of the enzyme include an esterase derived from an animal, preferably derived from an organ of an animal. Examples of the animal include pig, rabbit, bovine, equine, canine, and bird, and pig and rabbit are more preferred. Examples of the organ as the origin of the esterase include liver, pancreas, small intestine, stomach, and the like, and liver and pancreas are preferred. Preferred examples of the esterase include, for example, pig liver esterase, rabbit liver esterase, and the like.

Examples of such an esterase include, a protein consisting of the amino acid sequence shown in SEQ ID NO: 2 or 4, or a protein consisting of an amino acid sequence having 95% or more, preferably 97% or more, more preferably 99% or more identity to the amino acid sequence shown in SEQ ID NO: 2 or 4, and having an esterase activity similar to that of the aforementioned protein, and the like. Examples also include a protein encoded by a DNA consisting of the nucleotide sequence shown in SEQ ID NO: 1 or 3, or a protein encoded by a DNA consisting of a nucleotide sequence having 95% or more, preferably 97% or more, more preferably 99% or more identity to the nucleotide sequence shown in SEQ ID NO: 1 or 3, and having an esterase activity similar to that of the aforementioned protein, and the like.

The aforementioned enzyme may be an enzyme extracted from an organ of an animal, or an enzyme produced by using a recombinant DNA technique.

The aforementioned enzyme may be a purified enzyme or a crude enzyme. Further, the enzyme may also be an immobilized enzyme obtained by immobilizing such an enzyme as mentioned above on a carrier by an appropriate means. The carrier may be any carrier generally used. Examples include, for example, polysaccharides such as cellulose, agarose, dextran, κ-carrageenan, alginic acid, gelatin and cellulose acetate; natural polymers such as gluten; inorganic substances such as activated carbon, glass, white clay, kaolinite, alumina, silica gel, bentonite, hydroxyapatite and calcium phosphate; synthetic adsorbent materials such as polyacrylamide, polyvinyl acetate, polypropylene glycol and urethane, and the like. As the immobilization method, for example, the cross-linking method, physical adsorption method and entrapment can be used.

Examples of the buffer include phosphate buffer, acetate buffer, citrate buffer, borate buffer, Tris buffer, and the like, and preferred examples include phosphate buffer. Concentration of the buffer is 0.1 mmol/L to 1 mol/L, preferably 1 mmol/L to 100 mmol/L.

Examples of the metal salt include NaCl, $FeCl_3$, KCl, $CaCl_2$, $MgSO_4$, $MnSO_4$, $ZnCl_2$, $CoCl_2$, and the like. Concentration of the metal salt is preferably 0.01 to 10%.

The optically active carboxylic acid derivative of the formula (V) obtained by the aforementioned reaction can be separated by, after completion of the reaction, filtering the reaction mixture to remove insoluble matter, adding an acid to adjust the filtrate to pH 1 to 3, preferably about pH 2, and then extracting the reaction product with an appropriate solvent.

(Step 3)

(A) By reacting one equivalent to a large excess amount of a condensing agent with the compound (V) in a solvent at a temperature of −50 to 150° C., preferably −30 to 80° C., for 5 minutes to 72 hours, then adding 1 equivalent to a large excess amount of an ammonia source and allowing to react at a temperature of −50 to 150° C., preferably −30 to 80° C., for 5 minutes to 72 hours, (B) by reacting one equivalent to a large excess amount of an activating reagent with the compound (V) in a solvent at a temperature of −50 to 150° C., preferably −30 to 80° C., for 5 minutes to 72 hours, then adding one equivalent to a large excess amount of an ammonia source and allowing to react at a temperature of −50 to 150° C., preferably −30 to 80° C., for 5 minutes to 72 hours, or (C) by adding one equivalent to a large excess amount of an ammonia source to the compound (V) in a solvent at a temperature of −50 to 150° C., preferably 20 to 80° C., in the presence of 1 equivalent to a large excess amount of a condensing agent and allowing to react for 5 minutes to 72 hours, the compound (VI) can be obtained.

For all the cases of (A) to (C), any solvent that does not participate in the reaction may be used. Examples include, for example, cyclohexane, benzene, toluene, xylene, diethyl ether, diisopropyl ether, tert-butyl methyl ether, THF, dioxane, methyl acetate, ethyl acetate, butyl acetate, methyl isobutyl ketone, acetone, pyridine, DMF, DMSO, dichloromethane, chloroform, acetonitrile, and the like, and preferred examples include THF. These solvents can be used independently or as an arbitrary mixture.

For all the cases of (A) to (C), at the time of the reaction with the ammonia source, such a solvent as water, methanol, ethanol and isopropyl alcohol may be used, in addition to the aforementioned solvent, and these solvents may be used independently or as an arbitrary mixture.

For all the cases of (A) to (C), the reaction may also be performed by adding 1/10 to 30 equivalents of a base.

Examples of the base include an organic base and an inorganic base, and preferred examples include an organic base. Examples of the organic base include, for example 1,8-diazabicyclo[5,4,0]-7-undecene (DBU), triethylamine, 4-dimethylaminopyridine, N,N-dimethylaniline, pyridine, N-methylmorpholine, ethyldiisopropylamine, and the like, and preferred examples include triethylamine. Examples of the inorganic base include, for example, sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like. As the condensing agent, those condensing agents mentioned above can be similarly used. Also as the activation reagent and the ammonia source, those mentioned above can be similarly used.

(Step 4)

By allowing one equivalent to a large excess amount of a base to react on the compound (VI) in a solvent at a temperature of −50 to 150° C., preferably −20 to 60° C., for 5 minutes to 72 hours, the compound (I) or the compound (VII) can be obtained.

Examples of the solvent include cyclohexane, benzene, toluene, xylene, pyridine, diethyl ether, diisopropyl ether, tert-butyl methyl ether, THF, dioxane, water, isopropyl alcohol, methanol, ethanol, DMF, DMSO, and the like, and preferred examples include ethanol. These solvents can be used independently or as an arbitrary mixture.

Examples of the base include sodium hydride, sodium hydroxide, potassium hydroxide, sodium carbonate, sodium hydrogencarbonate, potassium carbonate, potassium hydrogencarbonate, cesium carbonate, sodium methoxide, sodium ethoxide, potassium tert-butoxide, and the like, and preferred examples include sodium ethoxide.

(Step 5)

When $R^{14}$ of the compound (VII) is an amino protected with a protective group that can be deprotected by hydrogenolysis, by adding a metal catalyst in an amount of 1/10 to 50% by weight, preferably 1 to 10% by weight, of the substrate in a solvent, and allowing to react at a temperature of −50 to 150° C., preferably 20 to 100° C., under a pressure of 1 to 10 atmospheres, preferably 1 to 5 atmospheres, for 5 minutes to 72 hours in the presence of hydrogen or a hydrogen donor, the compound (I) can be obtained.

Examples of the solvent include acetic acid, methyl acetate, ethyl acetate, butyl acetate, diethyl ether, diisopropyl ether, tert-butyl methyl ether, THF, dioxane, water, methanol, ethanol, isopropyl alcohol, DMF, and the like, and preferred examples include ethanol. These solvents can be used independently or as an arbitrary mixture.

Examples of the metal catalyst include platinum(IV) oxide, platinum/carbon, palladium(II) hydroxide, palladium (II) hydroxide/carbon, palladium/carbon, palladium/alumina, ruthenium/carbon, rhodium/carbon, rhodium/alumina, Wilkinson catalyst, Raney nickel, and the like, and preferred examples include palladium/carbon. Although palladium content in palladium/carbon is not particularly limited, it is preferably, for example, 5 to 10%.

Examples of the hydrogen donor include ammonium formate, cyclohexene, cyclohexa-1,3-diene, cyclohexa-1,4-diene, and the like.

When $R^{14}$ of the compound (VII) is an amino protected with a protective group that can be deprotected by an action of an acid, by allowing an acid to react on the protective group without solvent or in a solvent at a temperature of −50 to 150° C., preferably 20 to 100° C., the compound (I) can be obtained.

Examples of the solvent include cyclohexane, benzene, toluene, xylene, diethyl ether, diisopropyl ether, tert-butyl methyl ether, THF, dioxane, methyl acetate, ethyl acetate, butyl acetate, water, isopropyl alcohol, methanol, ethanol, DMF, dichloromethane, chloroform, and the like, and these solvent can be used independently or as an arbitrary mixture.

Examples of the acid include an inorganic acid, an organic acid, and the like, examples of the inorganic acid include hydrochloric acid, sulfuric acid, nitric acid, and the like, and examples of the organic acid include acetic acid, trifluoromethanesulfonic acid, trifluoroacetic acid, p-toluenesulfonic acid, and the like. Preferred examples include trifluoroacetic acid.

When $R^{14}$ of the compound (VII) is an amino protected with a protective group that can be deprotected by an action of a thiol, by allowing one equivalent to a large excess amount of a thiol to react on the protective group in a solvent at a temperature of −50 to 150° C., preferably 20 to 100° C., for 5 minutes to 72 hours in the presence of 1 equivalent to a large excess amount of a base, the compound (I) can be obtained.

Examples of the solvent include cyclohexane, benzene, toluene, xylene, pyridine, diethyl ether, THF, dioxane, methyl acetate, ethyl acetate, butyl acetate, water, acetone, isopropyl alcohol, methanol, ethanol, DMF, dichloromethane, chloroform, and the like, and these solvent can be used independently or as an arbitrary mixture.

As the thiol, any compound having sulfhydryl group can be used. Preferred examples include a thiophenol which may have a substituent and a lower alkyl thiol which may have a substituent, and more preferred examples include thiophenol, methanethiol, ethanethiol, 1-dodecanethiol, and the like.

Examples of the base include an organic base and an inorganic base. Examples of the organic base include, for example, DBU, triethylamine, 4-dimethylaminopyridine, N,N-dimethylaniline, pyridine, N-methylmorpholine, ethyldiisopropylamine, and the like, and examples of the inorganic base include, for example, sodium hydride, sodium hydroxide, potassium hydroxide, sodium carbonate, sodium hydrogencarbonate, potassium carbonate, potassium hydrogencarbonate, sodium methoxide, sodium ethoxide, potassium tert-butoxide, and the like, and preferred examples include potassium carbonate and triethylamine.

It is described in Non-patent document 3 that the compound (I) and the compound B:

[Formula 16]

(Compund B)

can be used as intermediates of the compound A, and accordingly, it is obvious to those skilled in the art that the compound (I) and the compound B can be used as raw materials for the production of compound A. According to the descriptions of the above literature, for example, each of the steps (b) to (e) of (15) mentioned above are performed as follows.

In the step (b), for example, a mixture of the compound B, about 1.5 equivalent of 2,5-dimethoxytetrahydrofuran and an excess amount of acetic acid is stirred at about 70° C. for about 1.5 hours. In a usual case, a crude reaction product can be isolated in a conventional manner, and this product can be used for the following step.

In the step (c), for example, a mixture of the product obtained in the aforementioned step (b), about 3 equivalents of trichloroacetyl chloride and an appropriate amount of chloroform is refluxed by heating for about 16 hours. Instead of chloroform, another inert solvent (for example, dichloromethane, THF, and the like) can also be used. In a usual case, a crude reaction product can be isolated in a conventional manner, and this product can be used for the following step.

In the step (d), for example, the product obtained in the aforementioned step (c), about 1.2 equivalents of 4-bromo-2-fluorobenzylamine hydrochloride, and about 2.5 equivalents of triethylamine are stirred at room temperature for about 16 hours in an appropriate amount of dry DMF solvent. In a usual case, a crude reaction product (the compound A) can be isolated in a conventional manner, and this product can be used for the following step.

In the step (e), for example, the compound A obtained in the step (d) is recrystallized from an appropriate amount of a mixed solvent of ethyl acetate and hexane. As other recrystallization solvents, alcohols such as ethanol can also be used.

EXAMPLES

Hereafter, the present invention will be more specifically explained with reference to examples and reference examples. However, the present invention is not limited to these examples.

The proton nuclear magnetic resonance ($^1$H NMR) spectra mentioned in the examples and the reference examples were measured at 300 MHz, and depending on the type of compound and measurement conditions, exchangeable proton may not be clearly observed. As indications of the multiplicity of signals, those usually used are applied, and "br" indicates a signal having an apparently large width. Furthermore, molecular weights of the compounds were confirmed by mass spectrometry (MS).

As for the conversion reaction from diethyl 2-benzyloxycarbonylamino-2-ethoxycarbonylsuccinate to (R)-1-ethyl hydrogen 3-benzyloxycarbonylamino-3-ethoxycarbonylsuccinate, content analysis was performed, and production amount was obtained as volume×content, and used to calculate the yield. The content analysis was performed by HPLC under the following conditions. More specifically, the column was Inertsil ODS-3 (φ4.6×75 mm, 3 μm) produced by GL Sciences Inc., the developing solvent was acetonitrile/0.05 mol/L phosphate buffer (pH 2.5)=50/50 (volume ratio), the flow rate was 1.0 mL/minute, the oven temperature was 40° C., and the detection wavelength was 254 nm. The content was determined by using a calibration curve prepared with standard solutions of known concentrations.

The optical purity analysis was performed by HPLC under the following conditions. As the column, CHIRALCEL OJ-RH (φ4.6×150 mm) produced by Daicel Chemical Industries, Ltd. was used. The optical purity analysis of 1-ethyl hydrogen 3-benzyloxycarbonylamino-3-ethoxycarbonylsuccinate was performed with acetonitrile/aqueous perchloric acid (pH 2.0)=30/70 (volume ratio) as the developing solvent at a flow rate of 1.0 mL/minute, oven temperature of 20° C., and detection wavelength of 254 nm. The optical purity analysis of diethyl 2-benzyloxycarbonylamino-2-carbamoylsuccinate was performed with acetonitrile/water=30/70 (volume ratio) as the developing solvent at a flow rate of 0.5 mL/minute, oven temperature of 20° C., and detection wavelength of 254 nm. The optical purity analysis of 2-benzyloxycarbonylamino-2-ethoxycarbonylsuccinimide was performed with acetonitrile/aqueous perchloric acid (pH 2.0)=30/70 (volume ratio) as the developing solvent at a flow rate of 0.5 mL/minute, oven temperature of 20° C., and detection wavelength of 254 nm. The optical purity analysis of (R)-2-amino-2-ethoxycarbonylsuccinimide was performed with aqueous perchloric acid (pH 1.0) as the developing solvent at a flow rate of 0.45 mL/minute, oven temperature of 5° C., and detection wavelength of 196 nm.

The intermediates and the objective compounds in the aforementioned production processes can be isolated and purified with separation and purification methods usually used in the synthetic organic chemistry, for example, filtration, extraction, washing, drying, concentration, recrystallization, various chromatography techniques, and the like. The intermediates may also be used for the subsequent reactions without particular purification.

In case a salt of the compound (I), (IV), (V), (VI), (VII) or (IV-A) is desired to be obtained, when the compound (I), (IV), (V), (VI), (VII) or (IV-A) is obtained in the form of salt, the salt per se may be purified, and when the compound (I), (IV), (V), (VI), (VII) or (IV-A) is obtained in a free form, the compound can be dissolved or suspended in an appropriate solvent, an acid or a base can be added to the solution or suspension, and a resulted salt can be separated and purified.

The compound (I), (IV), (V), (VI), (VII) or (IV-A), and a salt thereof may exist in the form of adduct with water or various solvents, and such adducts also fall within the scope of the present invention.

Example 1

Production of diethyl 2-benzyloxycarbonylamino-2-ethoxycarbonylsuccinate (Ethyl Chloroacetate Method)

A suspension of diethyl 2-benzyloxycarbonylaminomalonate (5.0 g), potassium carbonate (2.7 g), potassium iodide (0.27 g), and ethyl 2-chloroacetate (2.6 g) in DMF (50 mL) was stirred at 50° C. for 1 hour. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was crystallized from ethyl acetate/n-hexane to obtain the title compound (5.5 g, yield: 86%) as colorless crystals.

$^1$H NMR (CDCl$_3$) δ (ppm): 7.34 (5H, m), 6.39 (1H, s), 5.10 (2H, s), 4.24 (4H, q, J=6.9 Hz), 4.10 (2H, q, J=7.2 Hz), 3.49 (2H, s), 1.21 (9H, m)

MS (FAB): m/z 396 (M+H$^+$)

HR-MS (FAB): calcd for C$_{19}$H$_{26}$NO$_8$ 396.1658. found 396.1653 (M+H$^+$).

Example 2

Production of diethyl 2-benzyloxycarbonylamino-2-ethoxycarbonylsuccinate (Ethyl Bromoacetate Method)

A solution of diethyl 2-benzyloxycarbonylaminomalonate (50 g) in anhydrous DMF (300 mL) was added portionwise with sodium hydride (60%, 6.47 g) with ice cooling and stirring, then the mixture was stirred at room temperature for 30 minutes, and subsequently added with ethyl 2-bromoacetate (22.6 g), and the mixture was stirred overnight. The reaction mixture was poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, in which elution was performed with n-hexane/ethyl acetate (5:1) for purification, and then crystallized from ethyl acetate/n-hexane to obtain the title compound (46.7 g, yield: 83%) as colorless crystals.

Example 3

Production of (R)-1-ethyl hydrogen 3-benzyloxycarbonylamino-3-ethoxycarbonylsuccinate (Hydrolysis with Pig Liver Esterase)

4.0 g of pig liver esterase produced by Sigma [PLE (27 kU/g), lyophilized product, product number: E3019] was dissolved in a 0.05 mol/L phosphate buffer adjusted to pH 6.5 (360 mL), and the solution was added with a solution of diethyl 2-benzyloxycarbonylamino-2-ethoxycarbonylsuccinate (4.0 g) dissolved in ethanol (40 mL). The mixture was stirred at 30° C. for 20 hours to obtain (R)-1-ethyl hydrogen 3-benzyloxycarbonylamino-3-ethoxycarbonylsuccinate at a yield of 84% and optical purity of 93.6% ee.

After completion of the reaction, the reaction mixture was filtered by using a filtration aid (KC Floc 100) to remove the insoluble matter. The filtrate was cooled, and adjusted to pH 2 by adding 6 mol/L hydrochloric acid, then the objective substance was extracted with ethyl acetate, and the extract was washed with saturated brine, and dried over anhydrous magnesium sulfate. The solvent was evaporated under reduced pressure, and the residue was subjected to silica gel column chromatography, in which elution was performed with chloroform/methanol (10:1) for purification, to obtain the title compound (3.26 g, yield: 80%). Optical rotation $[α]_D^{28}$ was −0.6° (c 0.58, ethanol), and optical purity was 93.6% ee.

$^1$H NMR (CDCl$_3$) δ (ppm): 7.35 (5H, m), 6.51 (1H, s), 5.09 (2H, m), 4.24 (2H, q, J=7.2 Hz), 4.08 (2H, q, J=7.2 Hz), 3.48 (2H, s), 1.19 (6H, m)

MS (FAB): m/z 368 (M+H$^+$)

HR-MS (FAB): calcd for C$_{17}$H$_{22}$NO$_8$ 368.1345. found 368.1314 (M+H$^+$).

Example 4

Production of (R)-1-ethyl hydrogen 3-benzyloxycarbonylamino-3-ethoxycarbonylsuccinate (Hydrolysis with Rabbit Liver Esterase)

5 mg of rabbit liver esterase produced by Sigma (80 kU/g, lyophilized product, product number: E0887) was dissolved in a 0.05 mol/L phosphate buffer adjusted to pH 6.5 (0.4 mL), and the solution was added with a solution of diethyl 2-benzyloxycarbonylamino-2-ethoxycarbonylsuccinate (5 mg) dissolved in ethanol (0.05 mL). The mixture was stirred at 30° C. for 16 hours to obtain (R)-1-ethyl hydrogen 3-benzyloxycarbonylamino-3-ethoxycarbonylsuccinate at a yield of 52% and optical purity of 94.6% ee.

Example 5

Production of (R)-diethyl 2-benzyloxycarbonylamino-2-carbamoylsuccinate

A solution of (R)-1-ethyl hydrogen 3-benzyloxycarbonylamino-3-ethoxycarbonylsuccinate (1.8 g) in THF (20 mL) was added with triethylamine (0.96 mL) and isobutyl chloroformate (0.84 mL, 0.87 g) in this order at −15° C. with stirring, and the mixture was stirred for 5 minutes. A solution of 25% aqueous ammonia (0.47 mL) was dropped into the reaction mixture at the same temperature. The reaction mixture was stirred at the same temperature for 1 hour, and then poured into diluted hydrochloric acid, the mixture was extracted with ethyl acetate, and the extract was dried over anhydrous magnesium sulfate. The solvent was evaporated under reduced pressure, and the residue was subjected to silica gel column chromatography, in which elution was performed with n-hexane/ethyl acetate (1:1) for purification, and then crystallized from ethyl acetate/n-hexane to obtain the title compound (1.51 g, yield: 84%) as colorless crystals. Optical rotation $[\alpha]_D^{25}$ was −5.7° (c 0.52, ethanol) and optical purity was 96.1% ee.

$^1$H NMR (CDCl$_3$) δ (ppm): 7.34 (5H, m), 6.51 (1H, br), 6.35 (1H, br), 5.63 (1H, br), 5.12 (2H, s), 4.26 (2H, m), 4.10 (2H, q, J=7.2 Hz), 3.48 (2H, s), 1.23 (6H, m)

MS (FAB): 367 (M+H$^+$)

HR-MS (FAB): calcd for C$_{17}$H$_{23}$N$_2$O$_7$ 367.1505. found 367.1509 (M+H$^+$).

Example 6

Production of (R)-2-benzyloxycarbonylamino-2-ethoxycarbonylsuccinimide

A solution of (R)-diethyl 2-benzyloxycarbonylamino-2-carbamoylsuccinate (200 mg) in dehydrated ethanol (10 mL) was added with sodium ethoxide (41 mg) with ice cooling and stirring, the mixture was stirred at the same temperature for 2 hours, then cold 1 mol/L hydrochloric acid was poured into the mixture, and the mixture was extracted with ethyl acetate. The extract was washed with saturated brine, and then dried over anhydrous magnesium sulfate. The solvent was evaporated under reduced pressure, and the residue was recrystallized from ethyl acetate/n-hexane to obtain the title compound (149 mg, yield: 85%) as colorless crystals. Optical rotation $[\alpha]_D^{28}$ was −31.8° (c 0.59, ethanol), and optical purity was 99.2% ee.

$^1$H NMR (CDCl$_3$) δ (ppm): 8.39 (1H, s), 7.36 (5H, m), 6.27 (1H, s), 5.12 (2H, m), 4.32 (2H, q, J=6.9 Hz), 3.18 (2H, m), 1.29 (3H, t, J=7.1 Hz)

MS (FAB): 321 (M+H$^+$)

HR-MS (FAB): calcd for C$_{15}$H$_{17}$N$_2$O$_6$ 321.1087. found 321.1074 (M+H$^+$).

Example 7

Production of (R)-2-amino-2-ethoxycarbonylsuccinimide (R)-2-Benzyloxycarbonylamino-2-ethoxycarbonylsuccinimide (80 mg) was dissolved in ethanol (10 mL), the solution was added with 5% palladium/carbon (4 mg), and catalytic hydrogenation was performed at room temperature under a hydrogen atmosphere. After the catalyst was removed by filtration, the filtrate was concentrated under reduced pressure. The residue was recrystallized from ethanol to obtain the title compound (43 mg, yield: 93%) as colorless crystals. Optical rotation $[\alpha]_D^{24}$ was −35.9° (c 0.22, ethanol). Optical purity was more than 99.9% ee.

$^1$H NMR (CDCl$_3$) δ (ppm): 4.28 (2H, q, J=7.2 Hz), 3.19 (1H, d, J=18.0 Hz), 2.74 (1H, d, J=18.0 Hz), 1.30 (3H, t, J=7.1 Hz)

MS (FAB): 187 (M+H$^+$)

HR-MS (FAB): calcd for C$_7$H$_{11}$N$_2$O$_4$ 187.0719. found 187.0700 (M+H$^+$).

Example 8

The following compounds 1 to 4 were synthesized in the same manner as that of Example 2.

Production of Compound 1, diethyl 2-benzyloxycarbonylamino-2-(methoxycarbonylmethyl)malonate A suspension of diethyl 2-benzyloxycarbonylaminomalonate (3.0 g), potassium carbonate (1.6 g), potassium iodide (0.19 g), and methyl 2-bromoacetate (1.9 g) in DMF (50 mL) was stirred at 50° C. for 1 hour. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, in which elution was performed with n-hexane/ethyl acetate (4:1) for purification, and then crystallized from ethyl acetate/n-hexane to obtain the title compound (3.52 g, yield: 95%) as colorless oil.

$^1$H NMR (CDCl$_3$) δ (ppm): 7.34 (5H, m), 6.40 (1H, s), 5.09 (2H, s), 4.24 (4H, q, J=6.9 Hz), 3.64 (3H, s), 3.51 (2H, s), 1.22 (6H, m)

MS (FAB): m/z 382 (M+H$^+$)

Production of Compound 2, diethyl 2-benzyloxycarbonylamino-2-(isopropyloxycarbonylmethyl)malonate A suspension of diethyl 2-benzyloxycarbonylaminomalonate (5.0 g), potassium carbonate (2.7 g), potassium iodide (0.32 g), and isopropyl 2-bromoacetate (3.5 g) in DMF (50 mL) was stirred at 50° C. for 1 hour. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, and then purification was performed with n-hexane/ethyl acetate (5:1), to obtain the title compound (6.8 g, yield: 99%) as colorless oil.

$^1$H NMR (CDCl$_3$) δ (ppm): 7.33 (5H, m), 6.38 (1H, s), 5.10 (2H, s), 4.96 (1H, m), 4.24 (4H, q, J=6.9 Hz), 3.45 (2H, s), 1.23 (6H, m), 1.18 (6H, d, J=6.3 Hz)

MS (FAB): m/z 410 (M+H$^+$)

Production of Compound 3, diethyl 2-benzyloxycarbonylamino-2-(t-butoxycarbonylmethyl)malonate A suspension of diethyl 2-benzyloxycarbonylaminomalonate (5.0 g), potassium carbonate (2.7 g), potassium iodide (0.27 g), and t-butyl 2-bromoacetate (4.1 g) in DMF (50 mL) was stirred at 50° C. for 1 hour. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, and then purification was performed with n-hexane/ethyl acetate (5:1), to obtain the title compound (6.9 g, yield: 99%) as colorless oil.

$^1$H NMR (CDCl$_3$) δ (ppm): 7.34 (5H, m), 6.38 (1H, s), 5.10 (2H, s), 4.23 (4H, q, J=6.9 Hz), 3.40 (2H, s), 1.39 (9H, s), 1.22 (6H, t, J=7.1 Hz)

MS (FAB): m/z 424 (M+H$^+$)

Production of Compound 4, diethyl 2-benzyloxy-carbonylamino-2-(benzyloxycarbonylmethyl)malonate A solution of diethyl 2-benzyloxycarbonylaminomalonate (30 g) in anhydrous DMF (100 mL) was added portionwise with sodium hydride (60%, 4.27 g) with ice cooling and stirring, then the mixture was stirred at room temperature for 30 minutes, and then added with benzyl 2-bromoacetate (28.9 g), and the mixture was stirred overnight. The reaction mixture was poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, and then purification was performed with n-hexane/ethyl acetate (4:1), to obtain the title compound (43.9 g, yield: 99%) as colorless oil.

$^1$H NMR (CDCl$_3$) δ (ppm): 7.33 (10H, m), 6.39 (1H, s), 5.09 (4H, s), 4.20 (4H, q, J=6.9 Hz), 3.56 (2H, s), 1.23 (6H, m)

MS (FAB): m/z 458 (M+H$^+$)

Example 9

Compound 5: (R)-1-Methyl hydrogen 3-benzyloxycarbonylamino-3-ethoxycarbonylsuccinate 10 mg of pig liver esterase produced by Sigma [PLE (27 kU/g), lyophilized product, product number: E3019] was dissolved in a 0.1 mol/L phosphate buffer adjusted to pH 6.5 (0.9 mL), and the solution was added with a solution of the compound 1 (10 mg) dissolved in acetonitrile (0.1 mL). The mixture was stirred at 30° C. for 4 hours, and it was confirmed by HPLC that the compound 5 was obtained at a yield of 99.0%. The HPLC conditions were changed from those mentioned above, that is, methanol/water=60/40 (volume ratio, containing 0.1% trifluoroacetic acid) was used as the developing solvent, and the flow rate was 0.7 mL/minute. The product was confirmed by MS analysis. It was confirmed by HPLC (conditions were changed from those mentioned above, so that 40% acetonitrile was used as the developing solvent) that optical purity of the product was 93.1% ee.

MS (FAB): m/z 354 (M+H$^+$)

Example 10

The compounds 2 to 4 were reacted in the same manner as that of Example 9 to obtain the corresponding compounds 6 to 8.

Compound 6: (R)-1-Isopropyl hydrogen 3-benzyloxycarbonylamino-3-ethoxycarbonylsuccinate Example 11

Compound 7: (R)-1-t-Butyl hydrogen 3-benzyloxycarbonylamino-3-ethoxycarbonylsuccinate Example 12

Compound 8: (R)-1-Benzyl hydrogen 3-benzyloxycarbonylamino-3-ethoxycarbonylsuccinate Acetonitrile concentration of the developing solvent for the optical purity measurement was changed from the condition mentioned above, and the following conditions were used.
Example 10: 30% Acetonitrile
Example 11: 40% Acetonitrile
Example 12: 40% Acetonitrile The results are summarized below.

TABLE 1

| | Raw material | Product | Yield % | Optical purity % ee | MS (FAB): m/z |
|---|---|---|---|---|---|
| Example 10 | Compound 2 | Compound 6 | 97.4 | 97.4 | 382 (M + H+) |
| Example 11 | Compound 3 | Compound 7 | 98.5 | 97.9 | 396 (M + H$^+$) |
| Example 12 | Compound 4 | Compound 8 | 46.5 | 86.7 | 430 (M + H$^+$) |

Example 13

Production of diethyl 2-t-butyloxycarbonylamino-2-ethoxycarbonylsuccinate

A suspension of diethyl 2-t-butyloxycarbonylaminomalonate (5.0 g), potassium carbonate (3.0 g), and ethyl 2-bromoacetate (3.9 g) in DMF (20 mL) was stirred at 50° C. for 4 hours. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, and then purification was performed with n-hexane/ethyl acetate (5:1), to obtain the title compound (5.7 g, yield: 79%) as colorless oil.

$^1$H NMR (CDCl$_3$) δ (ppm): 6.13 (1H, s), 4.25 (4H, m), 4.12 (2H, q, J=6.9 Hz), 3.45 (2H, s), 1.43 (9H, s), 1.26 (9H, m)

MS (FAB): m/z 362 (M+H$^+$)

Example 14

Production of (R)-1-ethyl hydrogen 3-t-butyloxy-carbonylamino-3-ethoxycarbonylsuccinate (Hydrolysis with Pig Liver Esterase)

1.0 g of pig liver esterase produced by Sigma [PLE (27 kU/g), lyophilized product, product number: E3019] was dissolved in a 0.1 mol/L phosphate buffer adjusted to pH 7.5 (90 mL), and the solution was added with a solution of diethyl 2-t-butyloxycarbonylamino-2-ethoxycarbonylsuccinate (1.0 g) dissolved in acetonitrile (10 mL). The mixture was stirred at 30° C. for 4 hours to allow the reaction. After completion of the reaction, the reaction mixture was filtered by using a filtration aid (KC Floc 100) to remove the insoluble matter. The filtrate was cooled, and adjusted to pH 2 by adding 6 mol/L hydrochloric acid, then the objective substance was extracted with ethyl acetate, and the extract was washed with saturated brine, and dried over anhydrous magnesium sulfate. The solvent was evaporated under reduced pressure to obtain the title compound (1.0 g).

MS (FAB): m/z 334 (M+H$^+$)

Example 15

Production of (R)-diethyl 2-t-butyloxycarbonylamino-2-carbamoylsuccinate

A solution of (R)-1-ethyl hydrogen 3-t-butyloxycarbonylamino-3-ethoxycarbonylsuccinate (1.0 g) obtained in Example 14 in THF (20 mL) was added with triethylamine (0.62 mL) and isobutyl chloroformate (0.55 mL, 0.57 g) in this order at −15° C. with stirring, and the mixture was stirred for 30 minutes. A solution of 25% aqueous ammonia (0.30 mL) was dropped into the reaction mixture at the same temperature. The reaction mixture was stirred at the same temperature for 30 minutes, and then poured into diluted hydrochloric acid, the mixture was extracted with ethyl acetate, and then the extract was dried over anhydrous magnesium sulfate. The solvent was evaporated under reduced pressure, and the residue was subjected to silica gel column chromatography, in which elution was performed with n-hexane/ethyl acetate (1:1) for purification, and then crystallized from ethyl acetate/n-hexane to obtain the title compound (0.67 g, yield: 73%) as colorless crystals. Optical rotation $[\alpha]_D^{22}$ was +2.74° (c 0.50, ethanol).

$^1$H NMR (CDCl$_3$) δ (ppm): 6.42 (1H, br), 6.23 (1H, br), 5.50 (1H, br), 4.27 (2H, m), 4.14 (2H, q, J=7.2 Hz), 3.43 (2H, s), 1.44 (9H, s), 1.26 (6H, m)

MS (FAB): m/z 333 (M+H$^+$)

Example 16

Production of (R)-2-t-butyloxycarbonylamino-2-ethoxycarbonylsuccinimide (R)-diethyl 2-t-butyloxycarbonylamino-2-carbamoylsuccinate (590 mg) obtained in Example 15 was dissolved in acetone (6 mL) and water (6 mL), the solution was added with potassium carbonate (295 mg), the mixture was stirred for 6 hours, 1 mol/L hydrochloric acid was poured to the mixture, and the mixture was extracted with ethyl acetate. The extract was washed with saturated brine, and then dried over anhydrous magnesium sulfate. The solvent was evaporated under reduced pressure, and the residue was subjected to silica gel column chromatography, in which elution was performed with n-hexane/ethyl acetate (1:1) for purification, and then recrystallized from ethyl acetate/n-hexane to obtain the title compound (450 mg, yield: 88%) as colorless crystals. Optical rotation $[\alpha]_D^{25}$ was −39.1° (c 0.50, ethanol).

$^1$H NMR (CDCl$_3$) δ (ppm): 8.50 (1H, br), 5.99 (1H, br), 4.32 (2H, q, J=7.2 Hz), 3.16 (2H, m), 1.44 (9H, s), 1.30 (3H, t, J=7.2 Hz)

MS (FAB): m/z 287 (M+H$^+$)

Example 17

Production of (R)-2-amino-2-ethoxycarbonylsuccinimide hydrochloride (R)-2-t-Butyloxycarbonylamino-2-ethoxycarbonylsuccinimide (380 mg) obtained in Example 16 was dissolved in a 4 mol/L solution of hydrochloric acid in ethyl acetate (8 mL), and the reaction mixture was stirred for 1 hour, and then concentrated under reduced pressure. The residue was suspended in ether and filtered to obtain the title compound (288 mg, yield: 97%) as white crystals. Optical rotation $[\alpha]_D^{25}$ was −14.8° (c 1.0, methanol). Optical purity was 75.6% ee.

$^1$H NMR (DMSO-d$_6$) δ (ppm): 12.36 (1H, br), 9.65 (2H, br), 4.27 (2H, q, J=7.2 Hz), 3.34 (1H, d, J=18.2 Hz), 3.11 (1H, d, J=18.2 Hz), 1.20 (3H, t, J=7.2 Hz)

MS (FAB): m/z 187 (M+H$^+$)

Example 18

Production of diethyl 2-t-butyloxycarbonylamino-2-(benzyloxycarbonylmethyl)malonate A suspension of diethyl 2-t-butyloxycarbonylaminomalonate (5.0 g), potassium carbonate (3.0 g), and benzyl 2-bromoacetate (5.4 g) in DMF (20 mL) was stirred at 50° C. for 4 hours. The reaction mixture was cooled, and then poured into diluted hydrochloric acid, the mixture was extracted with ethyl acetate, and the extract was washed with saturated brine, and then dried over anhydrous magnesium sulfate. The solvent was evaporated under reduced pressure, and the residue was subjected to silica gel column chromatography, and then purification was performed with n-hexane/ethyl acetate (5:1), to obtain the title compound (6.5 g, yield: 85%) as colorless oil.

$^1$H NMR (CDCl$_3$) δ (ppm): 7.32 (5H, m), 6.1 (1H, s), 5.11 (2H, s), 4.21 (4H, m), 3.53 (2H, s), 1.41 (9H, s), 1.22 (6H, t, J=7.1 Hz)

MS (FAB): m/z 424 (M+H$^+$)

Example 19

Production of (R)-1-benzyl hydrogen 3-t-butyloxycarbonylamino-3-ethoxycarbonylsuccinate (Hydrolysis with Pig Liver Esterase)

1.0 g of pig liver esterase produced by Sigma [PLE (27 kU/g), lyophilized product, product number: E3019] was dissolved in a 0.1 mol/L phosphate buffer adjusted to pH 7.5 (90 mL), and the solution was added with a solution of diethyl 2-t-butyloxycarbonylamino-2-(benzyloxycarbonylmethyl)malonate (1.0 g) dissolved in acetonitrile (10 mL). The mixture was stirred at 30° C. for 4 hours to produce the title compound. Optical purity measured by HPLC was 78.1% ee. After completion of the reaction, the reaction mixture was filtered by using a filtration aid (KC Floc 100) to remove the insoluble matter. The filtrate was cooled, and adjusted to pH 2 by adding 6 mol/L hydrochloric acid, then the objective substance was extracted with ethyl acetate, and the extract was washed with saturated brine, and dried over anhydrous magnesium sulfate. The solvent was evaporated under reduced pressure to obtain the title compound (1.0 g).

MS (FAB): m/z 396 (M+H$^+$)

Example 20

Production of (R)-1-benzyl ethyl 3-t-butyloxycarbonylamino-3-carbamoylsuccinate

A solution of (R)-1-benzyl hydrogen 3-t-butyloxycarbonylamino-3-ethoxycarbonylsuccinate (1.0 g) obtained in Example 19 in THF (20 mL) was added with triethylamine (0.62 mL) and isobutyl chloroformate (0.55 mL, 0.57 g) in this order at −15° C. with stirring, and the mixture was stirred for 30 minutes. A solution of 25% aqueous ammonia (0.30 mL) was dropped into the reaction mixture at the same temperature. The reaction mixture was stirred at the same temperature for 30 minutes, and then poured into diluted hydrochloric acid, the mixture was extracted with ethyl acetate, and then the extract was dried over anhydrous magnesium sulfate. The solvent was evaporated under reduced pressure, and the residue was subjected to silica gel column chromatography, in which elution was performed with n-hexane/ethyl acetate (1:1) for purification, and then crystallized from ethyl acetate/n-hexane to obtain the title compound (0.60 g, yield: 55%) as colorless crystals. Optical rotation $[\alpha]_D^{25}$ was +1.28° (c 0.50, ethanol).

$^1$H NMR (CDCl$_3$) δ (ppm): 7.33 (5H, m), 6.39 (1H, br), 6.21 (1H, br), 5.56 (1H, br), 5.12 (2H, s), 4.22 (2H, q, J=7.2 Hz), 3.51 (2H, s), 1.41 (9H, s), 1.22 (3H, t, J=7.0 Hz)

MS (FAB): m/z 395 (M+H$^+$)

Example 21

Production of (R)-2-t-butyloxycarbonylamino-2-ethoxycarbonylsuccinimide (R)-1-Benzyl ethyl 3-t-butyloxycarbonylamino-3-carbamoylsuccinate (550 mg) obtained in Example 20 was dissolved in acetone (11 mL) and water (6 mL), the solution was added with potassium carbonate (231 mg), the mixture was stirred for 5 hours, and poured with 1 mol/L hydrochloric acid, and the mixture was extracted with ethyl acetate. The extract was washed with saturated brine, and then dried over anhydrous magnesium sulfate. The solvent was evaporated under reduced pressure, and the residue was subjected to silica gel column chromatography, in which elution was performed with n-hexane/ethyl acetate (1:1) for purification, and then recrystallized from ethyl acetate/n-hexane to obtain the title compound (358 mg, yield: 90%) as colorless crystals. Optical rotation $[\alpha]_D^{25}$ was −29.5° (c 0.50, ethanol).

$^1$H NMR (CDCl$_3$) δ (ppm): 8.33 (1H, br), 5.99 (1H, br), 4.32 (2H, q, J=7.2 Hz), 3.16 (2H, m), 1.44 (9H, s), 1.30 (3H, t, J=7.2 Hz)

MS (FAB): m/z 287 (M+H$^+$)

Example 22

Production of (R)-2-amino-2-ethoxycarbonylsuccinimide hydrochloride (R)-2-t-Butyloxycarbonylamino-2-ethoxycarbonylsuccinimide (243 mg) obtained in Example 21 was dissolved in a 4 mol/L solution of hydrochloric acid in ethyl acetate (5 mL), and the reaction mixture was stirred for 1 hour, and then concentrated under reduced pressure. The residue was suspended in ether, and filtered to obtain the title compound (179 mg, yield: 95%) as white crystals. Optical rotation $[\alpha]_D^{25}$ was −14.2° (c 1.0, methanol). Optical purity was 71.6% ee.

$^1$H NMR (DMSO-d$_6$) δ (ppm): 12.36 (1H, br), 9.65 (2H, br), 4.27 (2H, q, J=7.2 Hz), 3.34 (1H, d, J=18.2 Hz), 3.11 (1H, d, J=18.2 Hz), 1.20 (3H, t, J=7.2 Hz)

MS (FAB): m/z 187 (M+H$^+$)

INDUSTRIAL APPLICABILITY

According to the present invention, there are provided a process for producing optically active succinimide derivatives as key intermediates of the compound A, which is useful as a therapeutic agent for diabetic complications, as well as an ester derivative, an optically active carboxylic acid derivative, and an optically active amide derivative, which are useful intermediates of the compound A. There are also provided processes for producing these compounds and a process for producing the compound A by using the derivatives.

---

What is claimed is:

1. A process for producing compound A,

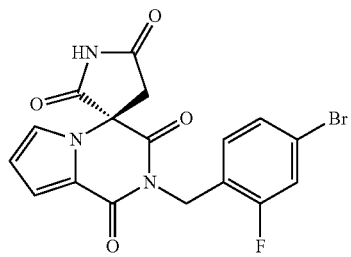

(Compound A)

or a salt thereof, said process comprises:
(A) reacting an ester derivative represented by formula (IV):

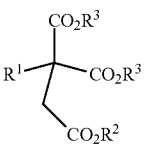

(IV)

or a salt thereof,

[wherein in said formula (IV), $R^1$ is an amino or an amino protected with a protective group and $R^2$ and $R^3$ are lower alkyls independently selected from the group consisting of methyl, ethyl, propyl, isopropyl, butyl, isobutyl, sec-butyl, tert-butyl, pentyl, isopentyl, neopentyl, and hexyl] with a pig liver esterase or a rabbit liver esterase for conversion of said ester derivative into an optically active carboxylic acid derivative represented by formula (V):

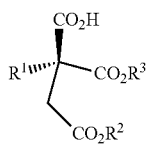

(V)

or a salt thereof,

[wherein in said formula (V), each of $R^1$, $R^2$, and $R^3$ has the same meaning as defined above];

(B) reacting said optically active carboxylic acid derivative represented by formula (V) or said salt thereof with (i) an ammonia source in the presence of a condensing agent, or (ii) an activating reagent to produce a resultant intermediate, and reacting said resultant intermediate with an ammonia source for conversion of said intermediate into an optically active amide derivative represented by formula (VI):

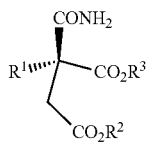

(VI)

or a salt thereof,

[wherein in said formula (VI), each of $R^1$, $R^2$, and $R^3$ has the same meaning as defined above];

(C1) when $R^1$ is an amino group, reacting said optically active amide derivative represented by formula (VI) or said salt thereof with a base for conversion of said optically active amide derivative into an optically active succinimide derivative represented by formula (I):

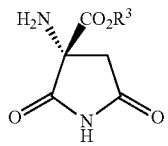

(I)

or a salt thereof,

[wherein in said formula (I), $R^3$ has the same meaning as defined above], or (C2) when $R^1$ is an amino protected with a protective group, reacting said optically active amide derivative represented by formula (VI) or said salt thereof with a base for conversion into an intermediate represented by formula (VII)

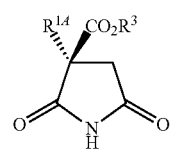

(VII)

or a salt thereof,

[wherein in said formula (VII), $R^{1A}$ is an amino protected with a protective group, and $R^3$ has the same meaning as defined above]; and eliminating said protective group of $R^{1A}$ on said intermediate represented by formula (VII) or salt thereof for conversion of said intermediate into an optically active succinimide derivative represented by formula (I):

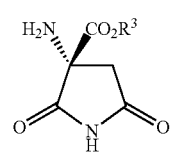

(I)

or a salt thereof,

[wherein in said formula (I), $R^3$ has the same meaning as defined above];

(D) reacting said optically active succinimide derivative of formula (I) with 2,5-dimethoxytetrahydrofuran with an acid to produce a first product;

(E) reacting said first product of step (D) with a trichloroacetylating reagent to produce a second product;

(F) reacting said second product of step (E) with 4-bromo-2-fluorobenzylamine to produce said compound A or said salt thereof; and (G) isolating said compound A or said salt thereof.

2. The process of claim 1, wherein $R^1$ is benzyloxycarbonylamino, $R^2$ is ethyl, and $R^3$ is ethyl.

3. The process of claim 1, wherein $R^3$ is ethyl.

4. The process of claim 1, wherein each of $R^1$ and $R^{1A}$ is benzyloxycarbonylamino.

5. The process of claim 1, further comprising reacting an aminomalonate derivative represented by formula (II):

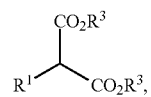

(II)

[wherein in said formula (II), $R^1$ and $R^3$ have the same meaning as defined above] with a halogenated acetic acid ester derivative represented by formula (III):

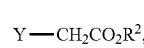

(III)

[wherein in said formula (III), $R^2$ has the same meaning as defined above; and Y is a halogen] in the presence of a base for conversion into said ester derivative represented by formula (IV):

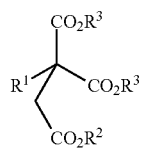
(IV)
or said salt thereof of step (A).
6. The process of claim 5, wherein $R^1$ is benzyloxycarbonylamino, $R^2$ is ethyl, and $R^3$ is ethyl.
7. The process of claim 5, wherein $R^3$ is ethyl.
8. The process of claim 5, wherein each of $R^1$ and $R^{1A}$ is benzyloxycarbonylamino.
* * * * *

SEQUENCE LISTING

```
<160> NUMBER OF SEQ ID NOS: 4

<210> SEQ ID NO 1
<211> LENGTH: 1701
<212> TYPE: DNA
<213> ORGANISM: Sus scrofa
<220> FEATURE:
<221> NAME/KEY: CDS
<222> LOCATION: (1)..(1701)

<400> SEQUENCE: 1 atg tgg ctt ctc ccg ctg gtc ctg acc tcc ctc gcc tct tct gca act      48
Met Trp Leu Leu Pro Leu Val Leu Thr Ser Leu Ala Ser Ser Ala Thr
1               5                   10                  15 tgg gca ggg cag cca gcc tcg ccg cct gtt gtg gac act gcc cag ggc      96
Trp Ala Gly Gln Pro Ala Ser Pro Pro Val Val Asp Thr Ala Gln Gly
            20                  25                  30 cga gtc ctg ggg aag tac gtc agc tta gaa ggc ctg gca cag ccg gtg     144
Arg Val Leu Gly Lys Tyr Val Ser Leu Glu Gly Leu Ala Gln Pro Val
        35                  40                  45
```

```
gcc gtc ttc ctg gga gtc cct ttt gcc aag ccc cct ctc gga tcc ttg      192
Ala Val Phe Leu Gly Val Pro Phe Ala Lys Pro Pro Leu Gly Ser Leu
    50              55                  60 agg ttt gct ccg ccg cag cct gca gaa cca tgg agc ttc gtg aag aac      240
Arg Phe Ala Pro Pro Gln Pro Ala Glu Pro Trp Ser Phe Val Lys Asn
65              70                  75                  80 acc acc tcc tac cct ccc atg tgc tgc cag gac cca gta gtg gag cag      288
Thr Thr Ser Tyr Pro Pro Met Cys Cys Gln Asp Pro Val Val Glu Gln
                85                  90                  95 atg acc tca gat cta ttt acc aac gga aag gag agg ctc act ctg gag      336
Met Thr Ser Asp Leu Phe Thr Asn Gly Lys Glu Arg Leu Thr Leu Glu
            100                 105                 110 ttt tct gaa gac tgt ctc tac cta aat att tac acc cct gct gac ctg      384
Phe Ser Glu Asp Cys Leu Tyr Leu Asn Ile Tyr Thr Pro Ala Asp Leu
        115                 120                 125 aca aag agg ggc aga ctg ccg gtg atg gtg tgg atc cac gga gga ggc      432
Thr Lys Arg Gly Arg Leu Pro Val Met Val Trp Ile His Gly Gly Gly
    130                 135                 140 ctg gtg ttg ggc ggg gca cca atg tat gat ggg gtg gtg ctt gct gcg      480
Leu Val Leu Gly Gly Ala Pro Met Tyr Asp Gly Val Val Leu Ala Ala
145                 150                 155                 160 cat gaa aac gtg gtg gtg gtg gcc atc cag tac cgc ctg ggc atc tgg      528
His Glu Asn Val Val Val Val Ala Ile Gln Tyr Arg Leu Gly Ile Trp
                165                 170                 175 gga ttc ttc agc aca ggg gat gaa cac agc cgg ggc aac tgg ggt cac      576
Gly Phe Phe Ser Thr Gly Asp Glu His Ser Arg Gly Asn Trp Gly His
            180                 185                 190 ttg gac cag gtg gcc gca ctg cac tgg gtc cag gag aac atc gcc aac      624
Leu Asp Gln Val Ala Ala Leu His Trp Val Gln Glu Asn Ile Ala Asn
        195                 200                 205 ttt gga ggc gac cca ggc tct gtg acc atc ttt gga gag tca gca gga      672
Phe Gly Gly Asp Pro Gly Ser Val Thr Ile Phe Gly Glu Ser Ala Gly
    210                 215                 220 ggg gaa agt gtc tct gtt ctg gtg ttg tct ccc ttg gcc aag aac ctc      720
Gly Glu Ser Val Ser Val Leu Val Leu Ser Pro Leu Ala Lys Asn Leu
225                 230                 235                 240 ttc cac cgg gcc atc tct gag agt ggc gtg gcc ctc act gtt gcc ctg      768
Phe His Arg Ala Ile Ser Glu Ser Gly Val Ala Leu Thr Val Ala Leu
                245                 250                 255 gtc agg aag gac atg aag gct gca gct aag caa att gct gtc ctt gct      816
Val Arg Lys Asp Met Lys Ala Ala Ala Lys Gln Ile Ala Val Leu Ala
            260                 265                 270 ggg tgt aaa acc acc acc tcg gct gtc ttt gtt cac tgc ctg cgc cag      864
Gly Cys Lys Thr Thr Thr Ser Ala Val Phe Val His Cys Leu Arg Gln
        275                 280                 285 aag tcg gag gac gag ctc ttg gac tta acg ctg aag atg aaa ttt tta      912
Lys Ser Glu Asp Glu Leu Leu Asp Leu Thr Leu Lys Met Lys Phe Leu
    290                 295                 300 act ctt gat ttt cat gga gac caa aga gag agc cat ccc ttc ctg ccc      960
Thr Leu Asp Phe His Gly Asp Gln Arg Glu Ser His Pro Phe Leu Pro
305                 310                 315                 320 act gtg gtg gat gga gtg ctg ctg ccc aag atg cct gaa gag att ctg     1008
Thr Val Val Asp Gly Val Leu Leu Pro Lys Met Pro Glu Glu Ile Leu
                325                 330                 335 gct gag aag gat ttc aac act gtc ccc tac atc gtg gga atc aac aag     1056
Ala Glu Lys Asp Phe Asn Thr Val Pro Tyr Ile Val Gly Ile Asn Lys
            340                 345                 350 caa gag ttt ggc tgg ctt ctg cca acg atg atg ggc ttc ccc ctc tct     1104
Gln Glu Phe Gly Trp Leu Leu Pro Thr Met Met Gly Phe Pro Leu Ser
        355                 360                 365
```

| | | | | | | | | | | | | | | | |
|---|---|---|---|---|---|---|---|---|---|---|---|---|---|---|---|
| gaa | ggc | aag | ctg | gac | cag | aag | acg | gcc | acg | tca | ctc | ctg | tgg | aag | tcc | 1152
| Glu | Gly | Lys | Leu | Asp | Gln | Lys | Thr | Ala | Thr | Ser | Leu | Leu | Trp | Lys | Ser |
| | 370 | | | | 375 | | | | 380 | | | | | | |

```
gaa ggc aag ctg gac cag aag acg gcc acg tca ctc ctg tgg aag tcc        1152
Glu Gly Lys Leu Asp Gln Lys Thr Ala Thr Ser Leu Leu Trp Lys Ser
    370                 375                 380 tac ccc atc gct aac atc cct gag gaa ctg act cca gtg gcc act gac        1200
Tyr Pro Ile Ala Asn Ile Pro Glu Glu Leu Thr Pro Val Ala Thr Asp
385                 390                 395                 400 aag tat ttg ggg ggg aca gac gac ccc gtc aaa aag aaa gac ctg ttc        1248
Lys Tyr Leu Gly Gly Thr Asp Asp Pro Val Lys Lys Lys Asp Leu Phe
                405                 410                 415 ctg gac ttg atg ggg gat gtg gtg ttt ggt gtc cca tct gtg acg gtg        1296
Leu Asp Leu Met Gly Asp Val Val Phe Gly Val Pro Ser Val Thr Val
                420                 425                 430 gcc cgt caa cac aga gat gca gga gcc ccc acc tac atg tat gag ttt        1344
Ala Arg Gln His Arg Asp Ala Gly Ala Pro Thr Tyr Met Tyr Glu Phe
            435                 440                 445 cag tat cgc cca agc ttc tca tcg gac aag aaa ccc aag acg gtg atc        1392
Gln Tyr Arg Pro Ser Phe Ser Ser Asp Lys Lys Pro Lys Thr Val Ile
        450                 455                 460 ggg gac cac ggg gat gag atc ttc tcc gtc ttt ggt ttt cca ctg tta        1440
Gly Asp His Gly Asp Glu Ile Phe Ser Val Phe Gly Phe Pro Leu Leu
465                 470                 475                 480 aaa ggc gat gcc cca gaa gag gag gtc agt ctc agc aag acg gtg atg        1488
Lys Gly Asp Ala Pro Glu Glu Glu Val Ser Leu Ser Lys Thr Val Met
                485                 490                 495 aaa ttc tgg gcc aac ttt gct cgc agt ggg aac ccc aat ggg gag ggg        1536
Lys Phe Trp Ala Asn Phe Ala Arg Ser Gly Asn Pro Asn Gly Glu Gly
            500                 505                 510 ctg ccc cat tgg ccg atg tac gac cag gaa gaa ggg tac ctt cag atc        1584
Leu Pro His Trp Pro Met Tyr Asp Gln Glu Glu Gly Tyr Leu Gln Ile
        515                 520                 525 ggc gtc aac acc cag gca gcc aag agg ctg aaa ggt gaa gaa gtg gcc        1632
Gly Val Asn Thr Gln Ala Ala Lys Arg Leu Lys Gly Glu Glu Val Ala
    530                 535                 540 ttc tgg aac gat ctc ctg tcc aag gag gca gca aag aag cca ccc aag        1680
Phe Trp Asn Asp Leu Leu Ser Lys Glu Ala Ala Lys Lys Pro Pro Lys
545                 550                 555                 560 ata aag cat gct gag ctg tga                                            1701
Ile Lys His Ala Glu Leu
                565

<210> SEQ ID NO 2
<211> LENGTH: 566
<212> TYPE: PRT
<213> ORGANISM: Sus scrofa

<400> SEQUENCE: 2

Met Trp Leu Leu Pro Leu Val Leu Thr Ser Leu Ala Ser Ser Ala Thr
1               5                   10                  15

Trp Ala Gly Gln Pro Ala Ser Pro Pro Val Val Asp Thr Ala Gln Gly
            20                  25                  30

Arg Val Leu Gly Lys Tyr Val Ser Leu Glu Gly Leu Ala Gln Pro Val
        35                  40                  45

Ala Val Phe Leu Gly Val Pro Phe Ala Lys Pro Pro Leu Gly Ser Leu
    50                  55                  60

Arg Phe Ala Pro Pro Gln Pro Ala Glu Pro Trp Ser Phe Val Lys Asn
65                  70                  75                  80

Thr Thr Ser Tyr Pro Pro Met Cys Cys Gln Asp Pro Val Val Glu Gln
                85                  90                  95
```

-continued

```
Met Thr Ser Asp Leu Phe Thr Asn Gly Lys Glu Arg Leu Thr Leu Glu
            100                 105                 110

Phe Ser Glu Asp Cys Leu Tyr Leu Asn Ile Tyr Thr Pro Ala Asp Leu
        115                 120                 125

Thr Lys Arg Gly Arg Leu Pro Val Met Val Trp Ile His Gly Gly Gly
    130                 135                 140

Leu Val Leu Gly Gly Ala Pro Met Tyr Asp Gly Val Val Leu Ala Ala
145                 150                 155                 160

His Glu Asn Val Val Val Ala Ile Gln Tyr Arg Leu Gly Ile Trp
                165                 170                 175

Gly Phe Phe Ser Thr Gly Asp Glu His Ser Arg Gly Asn Trp Gly His
            180                 185                 190

Leu Asp Gln Val Ala Ala Leu His Trp Val Gln Glu Asn Ile Ala Asn
        195                 200                 205

Phe Gly Gly Asp Pro Gly Ser Val Thr Ile Phe Gly Glu Ser Ala Gly
    210                 215                 220

Gly Glu Ser Val Ser Val Leu Val Leu Ser Pro Leu Ala Lys Asn Leu
225                 230                 235                 240

Phe His Arg Ala Ile Ser Glu Ser Gly Val Ala Leu Thr Val Ala Leu
                245                 250                 255

Val Arg Lys Asp Met Lys Ala Ala Lys Gln Ile Ala Val Leu Ala
            260                 265                 270

Gly Cys Lys Thr Thr Thr Ser Ala Val Phe Val His Cys Leu Arg Gln
        275                 280                 285

Lys Ser Glu Asp Glu Leu Leu Asp Leu Thr Leu Lys Met Lys Phe Leu
    290                 295                 300

Thr Leu Asp Phe His Gly Asp Gln Arg Glu Ser His Pro Phe Leu Pro
305                 310                 315                 320

Thr Val Val Asp Gly Val Leu Pro Lys Met Pro Glu Glu Ile Leu
                325                 330                 335

Ala Glu Lys Asp Phe Asn Thr Val Pro Tyr Ile Val Gly Ile Asn Lys
            340                 345                 350

Gln Glu Phe Gly Trp Leu Leu Pro Thr Met Met Gly Phe Pro Leu Ser
        355                 360                 365

Glu Gly Lys Leu Asp Gln Lys Thr Ala Thr Ser Leu Leu Trp Lys Ser
    370                 375                 380

Tyr Pro Ile Ala Asn Ile Pro Glu Glu Leu Thr Pro Val Ala Thr Asp
385                 390                 395                 400

Lys Tyr Leu Gly Gly Thr Asp Pro Val Lys Lys Asp Leu Phe
                405                 410                 415

Leu Asp Leu Met Gly Asp Val Val Phe Gly Val Pro Ser Val Thr Val
            420                 425                 430

Ala Arg Gln His Arg Asp Ala Gly Ala Pro Thr Tyr Met Tyr Glu Phe
        435                 440                 445

Gln Tyr Arg Pro Ser Phe Ser Ser Asp Lys Pro Lys Thr Val Ile
    450                 455                 460

Gly Asp His Gly Asp Glu Ile Phe Ser Val Phe Gly Phe Pro Leu Leu
465                 470                 475                 480

Lys Gly Asp Ala Pro Glu Glu Val Ser Leu Ser Lys Thr Val Met
                485                 490                 495

Lys Phe Trp Ala Asn Phe Ala Arg Ser Gly Asn Pro Asn Gly Glu Gly
            500                 505                 510

Leu Pro His Trp Pro Met Tyr Asp Gln Glu Glu Gly Tyr Leu Gln Ile
```

|  |  | 515 |  |  |  | 520 |  |  |  | 525 |  |
| --- | --- | --- | --- | --- | --- | --- | --- | --- | --- | --- | --- |

Gly Val Asn Thr Gln Ala Ala Lys Arg Leu Lys Gly Glu Glu Val Ala
       530                535              540

Phe Trp Asn Asp Leu Leu Ser Lys Glu Ala Ala Lys Lys Pro Pro Lys
545                   550               555            560

Ile Lys His Ala Glu Leu
       565

<210> SEQ ID NO 3
<211> LENGTH: 1698
<212> TYPE: DNA
<213> ORGANISM: Oryctolagus cuniculus
<220> FEATURE:
<221> NAME/KEY: CDS
<222> LOCATION: (1)..(1698)

<400> SEQUENCE: 3

| atg tgg ctc tgt gca ttg gcc ctg gcc tct ctc gcc gct tgc acg gct | 48 |
| --- | --- |
| Met Trp Leu Cys Ala Leu Ala Leu Ala Ser Leu Ala Ala Cys Thr Ala |  |
| 1                5               10              15 |  |
| tgg ggg cac ccg tct gca cca cct gtg gta gat act gtg cat ggc aaa | 96 |
| Trp Gly His Pro Ser Ala Pro Pro Val Val Asp Thr Val His Gly Lys |  |
|           20                 25              30 |  |
| gtc ctg ggg aag ttc gtc agc tta gaa gga ttt gca cag ccc gtg gcc | 144 |
| Val Leu Gly Lys Phe Val Ser Leu Glu Gly Phe Ala Gln Pro Val Ala |  |
|         35               40              45 |  |
| gtc ttc ctg gga gtc ccc ttc gcc aag ccc cct ctt gga tcc ctg agg | 192 |
| Val Phe Leu Gly Val Pro Phe Ala Lys Pro Pro Leu Gly Ser Leu Arg |  |
|      50               55               60 |  |
| ttt gca cca cca cag cct gca gaa tca tgg agc cac gtg aag aac acc | 240 |
| Phe Ala Pro Pro Gln Pro Ala Glu Ser Trp Ser His Val Lys Asn Thr |  |
| 65                70              75              80 |  |
| acc tcc tac cct ccc atg tgc tcc cag gac gca gta tca ggg cat atg | 288 |
| Thr Ser Tyr Pro Pro Met Cys Ser Gln Asp Ala Val Ser Gly His Met |  |
|                 85               90              95 |  |
| ctc tcg gag ctc ttc acc aac aga aaa gag aac atc cct ctt aag ttt | 336 |
| Leu Ser Glu Leu Phe Thr Asn Arg Lys Glu Asn Ile Pro Leu Lys Phe |  |
|             100              105             110 |  |
| tct gaa gac tgc ctt tac ctg aat att tac acc cct gct gac ctg aca | 384 |
| Ser Glu Asp Cys Leu Tyr Leu Asn Ile Tyr Thr Pro Ala Asp Leu Thr |  |
|         115             120             125 |  |
| aag aga ggc agg ctg ccg gtg atg gtg tgg atc cat gga ggt ggt ctg | 432 |
| Lys Arg Gly Arg Leu Pro Val Met Val Trp Ile His Gly Gly Gly Leu |  |
|     130               135              140 |  |
| atg gtg ggt gga gca tca acc tat gat ggc ctg gct ctt tct gcc cat | 480 |
| Met Val Gly Gly Ala Ser Thr Tyr Asp Gly Leu Ala Leu Ser Ala His |  |
| 145               150              155            160 |  |
| gag aac gtg gtg gtg gtg acc att cag tac cgc ctg ggc atc tgg gga | 528 |
| Glu Asn Val Val Val Val Thr Ile Gln Tyr Arg Leu Gly Ile Trp Gly |  |
|                 165             170             175 |  |
| ttc ttc agc aca gga gat gag cac agc cga ggg aac tgg ggt cac ttg | 576 |
| Phe Phe Ser Thr Gly Asp Glu His Ser Arg Gly Asn Trp Gly His Leu |  |
|             180             185             190 |  |
| gac cag gtg gct gcg ctg cgg tgg gtc cag gac aac att gcc aac ttt | 624 |
| Asp Gln Val Ala Ala Leu Arg Trp Val Gln Asp Asn Ile Ala Asn Phe |  |
|         195             200             205 |  |
| gga ggg gac cca ggc tct gtg acc atc ttt gga gag tca gca gga ggt | 672 |
| Gly Gly Asp Pro Gly Ser Val Thr Ile Phe Gly Glu Ser Ala Gly Gly |  |
|     210               215              220 |  |
| caa agt gtc tct atc ctt cta tta tcc ccc ctg acc aag aat ctc ttc | 720 |

```
           Gln Ser Val Ser Ile Leu Leu Leu Ser Pro Leu Thr Lys Asn Leu Phe
           225                 230                 235                 240 cat cga gca att tcc gag agt ggc gtg gcc ctc ctt tcc agt ctc ttc       768
His Arg Ala Ile Ser Glu Ser Gly Val Ala Leu Leu Ser Ser Leu Phe
                    245                 250                 255 agg aag aac acc aag tcc ttg gct gag aaa att gcc atc gaa gct ggg       816
Arg Lys Asn Thr Lys Ser Leu Ala Glu Lys Ile Ala Ile Glu Ala Gly
                260                 265                 270 tgt aaa acc acc acc tcg gct gtc atg gtt cac tgc ctg cgc cag aag       864
Cys Lys Thr Thr Thr Ser Ala Val Met Val His Cys Leu Arg Gln Lys
            275                 280                 285 aca gag gaa gaa ctc atg gag gtg aca ttg aaa atg aaa ttt atg gct       912
Thr Glu Glu Glu Leu Met Glu Val Thr Leu Lys Met Lys Phe Met Ala
        290                 295                 300 cta gat cta gtt ggc gac ccc aaa gag aac acc gcc ttc ctg acc act       960
Leu Asp Leu Val Gly Asp Pro Lys Glu Asn Thr Ala Phe Leu Thr Thr
305                 310                 315                 320 gtg att gat ggg gtg ctg ctg cca aaa gca cct gca gag att ctg gca      1008
Val Ile Asp Gly Val Leu Leu Pro Lys Ala Pro Ala Glu Ile Leu Ala
                    325                 330                 335 gag aag aaa tac aac atg ctg ccc tac atg gtg gga atc aac cag caa      1056
Glu Lys Lys Tyr Asn Met Leu Pro Tyr Met Val Gly Ile Asn Gln Gln
                340                 345                 350 gag ttt ggc tgg att atc cca atg caa atg ctg ggc tat cca ctc tct      1104
Glu Phe Gly Trp Ile Ile Pro Met Gln Met Leu Gly Tyr Pro Leu Ser
            355                 360                 365 gaa ggc aaa ctg gac cag aag aca gct aca gaa ctc ttg tgg aag tcc      1152
Glu Gly Lys Leu Asp Gln Lys Thr Ala Thr Glu Leu Leu Trp Lys Ser
        370                 375                 380 tac ccc att gtc aat gtc tct aag gag ctg act cca gtg gcc act gag      1200
Tyr Pro Ile Val Asn Val Ser Lys Glu Leu Thr Pro Val Ala Thr Glu
385                 390                 395                 400 aag tat tta gga ggg aca gat gac cct gtc aaa aag aaa gac ttg ttc      1248
Lys Tyr Leu Gly Gly Thr Asp Asp Pro Val Lys Lys Lys Asp Leu Phe
                    405                 410                 415 ctg gac atg ctt gca gat ttg tta ttt ggt gtc cca tct gtg aat gtg      1296
Leu Asp Met Leu Ala Asp Leu Leu Phe Gly Val Pro Ser Val Asn Val
                420                 425                 430 gct cgt cac cac aga gat gct gga gcc ccc acc tat atg tat gag tat      1344
Ala Arg His His Arg Asp Ala Gly Ala Pro Thr Tyr Met Tyr Glu Tyr
            435                 440                 445 cgg tat cgc cca agc ttc tca tca gac atg aga ccc aag aca gtg ata      1392
Arg Tyr Arg Pro Ser Phe Ser Ser Asp Met Arg Pro Lys Thr Val Ile
        450                 455                 460 ggg gac cat gga gat gag atc ttc tct gtc tta gga gcc ccg ttt tta      1440
Gly Asp His Gly Asp Glu Ile Phe Ser Val Leu Gly Ala Pro Phe Leu
465                 470                 475                 480 aaa gag ggt gcc aca gaa gag gag atc aaa ctg agc aag atg gtg atg      1488
Lys Glu Gly Ala Thr Glu Glu Glu Ile Lys Leu Ser Lys Met Val Met
                    485                 490                 495 aaa tac tgg gcc aac ttt gct agg aat ggg aat ccc aat gga gaa ggg      1536
Lys Tyr Trp Ala Asn Phe Ala Arg Asn Gly Asn Pro Asn Gly Glu Gly
                500                 505                 510
```

```
ctt cct caa tgg cca gca tat gac tac aag gaa ggt tac ctg cag att    1584
Leu Pro Gln Trp Pro Ala Tyr Asp Tyr Lys Glu Gly Tyr Leu Gln Ile
    515                 520                 525 gga gcc acc acc cag gca gcc cag aaa ctg aaa gac aag gaa gtg gct    1632
Gly Ala Thr Thr Gln Ala Ala Gln Lys Leu Lys Asp Lys Glu Val Ala
530                 535                 540 ttc tgg act gag ctc tgg gcc aag gag gca gca agg cca cgt gag aca    1680
Phe Trp Thr Glu Leu Trp Ala Lys Glu Ala Ala Arg Pro Arg Glu Thr
545                 550                 555                 560 gag cac att gag ctg tga                                            1698
Glu His Ile Glu Leu
                565

<210> SEQ ID NO 4
<211> LENGTH: 565
<212> TYPE: PRT
<213> ORGANISM: Oryctolagus cuniculus

<400> SEQUENCE: 4

Met Trp Leu Cys Ala Leu Ala Leu Ala Ser Leu Ala Ala Cys Thr Ala
1               5                   10                  15

Trp Gly His Pro Ser Ala Pro Val Val Asp Thr Val His Gly Lys
                20                  25                  30

Val Leu Gly Lys Phe Val Ser Leu Glu Gly Phe Ala Gln Pro Val Ala
            35                  40                  45

Val Phe Leu Gly Val Pro Phe Ala Lys Pro Pro Leu Gly Ser Leu Arg
        50                  55                  60

Phe Ala Pro Pro Gln Pro Ala Glu Ser Trp Ser His Val Lys Asn Thr
65                  70                  75                  80

Thr Ser Tyr Pro Pro Met Cys Ser Gln Asp Ala Val Ser Gly His Met
                85                  90                  95

Leu Ser Glu Leu Phe Thr Asn Arg Lys Glu Asn Ile Pro Leu Lys Phe
            100                 105                 110

Ser Glu Asp Cys Leu Tyr Leu Asn Ile Tyr Thr Pro Ala Asp Leu Thr
        115                 120                 125

Lys Arg Gly Arg Leu Pro Val Met Val Trp Ile His Gly Gly Gly Leu
130                 135                 140

Met Val Gly Gly Ala Ser Thr Tyr Asp Gly Leu Ala Leu Ser Ala His
145                 150                 155                 160

Glu Asn Val Val Val Thr Ile Gln Tyr Arg Leu Gly Ile Trp Gly
                165                 170                 175

Phe Phe Ser Thr Gly Asp Glu His Ser Arg Gly Asn Trp Gly His Leu
            180                 185                 190

Asp Gln Val Ala Ala Leu Arg Trp Val Gln Asp Asn Ile Ala Asn Phe
        195                 200                 205

Gly Gly Asp Pro Gly Ser Val Thr Ile Phe Gly Glu Ser Ala Gly Gly
210                 215                 220

Gln Ser Val Ser Ile Leu Leu Ser Pro Leu Thr Lys Asn Leu Phe
225                 230                 235                 240

His Arg Ala Ile Ser Glu Ser Gly Val Ala Leu Leu Ser Ser Leu Phe
                245                 250                 255

Arg Lys Asn Thr Lys Ser Leu Ala Glu Lys Ile Ala Ile Glu Ala Gly
            260                 265                 270

Cys Lys Thr Thr Thr Ser Ala Val Met Val His Cys Leu Arg Gln Lys
        275                 280                 285
```

```
Thr Glu Glu Glu Leu Met Glu Val Thr Leu Lys Met Lys Phe Met Ala
    290                 295                 300
Leu Asp Leu Val Gly Asp Pro Lys Glu Asn Thr Ala Phe Leu Thr Thr
305                 310                 315                 320
Val Ile Asp Gly Val Leu Leu Pro Lys Ala Pro Ala Glu Ile Leu Ala
                325                 330                 335
Glu Lys Lys Tyr Asn Met Leu Pro Tyr Met Val Gly Ile Asn Gln Gln
                340                 345                 350
Glu Phe Gly Trp Ile Ile Pro Met Gln Met Leu Gly Tyr Pro Leu Ser
            355                 360                 365
Glu Gly Lys Leu Asp Gln Lys Thr Ala Thr Glu Leu Leu Trp Lys Ser
    370                 375                 380
Tyr Pro Ile Val Asn Val Ser Lys Glu Leu Thr Pro Val Ala Thr Glu
385                 390                 395                 400
Lys Tyr Leu Gly Gly Thr Asp Asp Pro Val Lys Lys Asp Leu Phe
                405                 410                 415
Leu Asp Met Leu Ala Asp Leu Leu Phe Gly Val Pro Ser Val Asn Val
            420                 425                 430
Ala Arg His His Arg Asp Ala Gly Ala Pro Thr Tyr Met Tyr Glu Tyr
        435                 440                 445
Arg Tyr Arg Pro Ser Phe Ser Ser Asp Met Arg Pro Lys Thr Val Ile
    450                 455                 460
Gly Asp His Gly Asp Glu Ile Phe Ser Val Leu Gly Ala Pro Phe Leu
465                 470                 475                 480
Lys Glu Gly Ala Thr Glu Glu Glu Ile Lys Leu Ser Lys Met Val Met
                485                 490                 495
Lys Tyr Trp Ala Asn Phe Ala Arg Asn Gly Asn Pro Asn Gly Glu Gly
            500                 505                 510
Leu Pro Gln Trp Pro Ala Tyr Asp Tyr Lys Glu Gly Tyr Leu Gln Ile
        515                 520                 525
Gly Ala Thr Thr Gln Ala Ala Gln Lys Leu Lys Asp Lys Glu Val Ala
    530                 535                 540
Phe Trp Thr Glu Leu Trp Ala Lys Glu Ala Ala Arg Pro Arg Glu Thr
545                 550                 555                 560
Glu His Ile Glu Leu
                565
```